United States Patent [19]

Püschner et al.

[11] Patent Number: 5,380,077

[45] Date of Patent: Jan. 10, 1995

[54] MACHINING DEVICE FOR MACHINING PRECISION, IN PARTICULAR DENTAL, WORKPIECES IN A MACHINING CHAMBER SURROUNDED BY A HOUSING

[75] Inventors: Georg Püschner, Leutkirch; Herbert Lott, Bad Wruzach, both of Germany

[73] Assignee: Kaltenbach & Voigt GmbH & Co., Biberach Rib, Germany

[21] Appl. No.: 910,576

[22] Filed: Jul. 8, 1992

[30] Foreign Application Priority Data

Jul. 11, 1991 [DE] Germany .................... 4123014

[51] Int. Cl.6 .................... A61G 11/00; A61B 19/02
[52] U.S. Cl. .................... 312/1; 312/209
[58] Field of Search .................... 312/209, 135, 114; 2/16, 159; 74/17.8; 220/85; 285/189; 128/113, 132

[56] References Cited

U.S. PATENT DOCUMENTS

| | | | |
|---|---|---|---|
| 3,035,315 | 5/1962 | Saunders | 312/1 X |
| 3,875,927 | 4/1975 | Trexler | 128/1 B |
| 3,907,389 | 9/1975 | Cox et al. | 312/1 |
| 4,141,609 | 2/1979 | Eisert | 128/1 B |
| 4,251,123 | 2/1981 | Brackenbush et al. | 312/1 |
| 4,960,143 | 10/1990 | Dore, Jr. et al. | 312/1 X |

*Primary Examiner*—Ralph A. Lewis
*Assistant Examiner*—Nancy Mulcare
*Attorney, Agent, or Firm*—Wood, Phillips, VanSanten, Hoffman & Ertel

[57] ABSTRACT

Machining device for machining precision, in particular dental, workpieces in a machining chamber surrounded by a housing.

In a machining device for machining precision, in particular dental, workpieces in a machining chamber surrounded by a housing, having an inspection window with two gripping holes arranged to the two sides of the inspection window, a mounting for a glove or sleeve being arranged in the edge regions of each hole, the mounting has two coaxial clamping rings insertable one into the other, of which the one clamping ring is affixed to the housing in the region of the associated hole edge.

12 Claims, 10 Drawing Sheets

MACHINING DEVICE FOR MACHINING PRECISION, IN PARTICULAR DENTAL, WORKPIECES IN A MACHINING CHAMBER SURROUNDED BY A HOUSING

TECHNICAL FIELD OF THE INVENTION

The invention relates to a machining device for machining precision, in particular dental, workpieces in a machining chamber surrounded by a housing.

BACKGROUND OF THE INVENTION AND PRIOR ART

In the machining chamber of a machining device of this kind, workpieces are blasted by means of a compressed air-blasting medium mixture. This type of machining can easily lead to injury to the person performing it and is also health hazardous in particular if the workpieces contain hazardous substances as is the case, for example, with quartz (danger of silicosis). This material is often used, in particular with dental workpieces. In the machining chamber these types of machinings can be carried out so that they are safe for the operator and the environment because, on the one hand, the machining chamber is closed—which purpose is served by gloves or sleeves in the region of the gripping holes, the collar rings of the gloves or sleeves each being secured in a mounting provided on the edge of the opening. In modern machining devices the machining chamber can be connected to a suction device by means of which the dust, in particular health hazardous dust, e.g. quartz dust, can be sucked off and collected.

With the known mountings for securing the gloves or sleeves, installation is awkward. A great deal of work is thus necessary to exchange the gloves or sleeves or replace them with new ones. In practice this leads the operator to avoid and therefore refrain from doing this, which results in some types of machining being carried out improperly which is not only dangerous but can also impair the quality of machining.

OBJECT OF THE INVENTION

It is the object of the invention to provide a machining device of the kind mentioned in the introduction so that the gloves or sleeves can be mounted and dismounted easily and quickly while ensuring reliable securement.

SUMMARY OF THE INVENTION

According to the invention there is provided a machining device for machining precision, in particular dental, workpieces in a machining chamber surrounded by a housing, having an inspection window with two gripping holes arranged to the two sides of the inspection window, a mounting for a glove or sleeve being arranged in the edge regions of each hole, wherein the mounting has two coaxial clamping rings insertable one into the other, of which the one clamping ring is affixed to the housing in the region of the associated hole edge.

In the machining device according to the invention, for securing the collar edge regions of the gloves or sleeves, two clamping rings are provided that can be inserted into one another coaxially, and owing to the clamping effect ensure a rigid and reliable connection. The clamping rings can be clamped and unclamped in a ready and quick manner because only the clamping effect is to be brought about, or is to be overcome when releasing. Further measures for releasing, e.g. undoing screws or other fastening elements, are not necessary. In the embodiment according to the invention a glove or a sleeve can therefore be simply and quickly affixed or detached and thus exchanged or replaced.

Embodiments of the invention have further features characterised in particular by improvement of the clamping effect and ease of use. Furthermore the further developments leads to simple solutions which make economical manufacture possible.

BRIEF DESCRIPTION OF THE DRAWINGS

The invention will now be described in more detail with reference to preferred exemplary embodiments shown in the drawings, in which.

DETAILED DESCRIPTION OF PREFERRED EXEMPLARY EMBODIMENTS OF THE INVENTION

Figure 2:
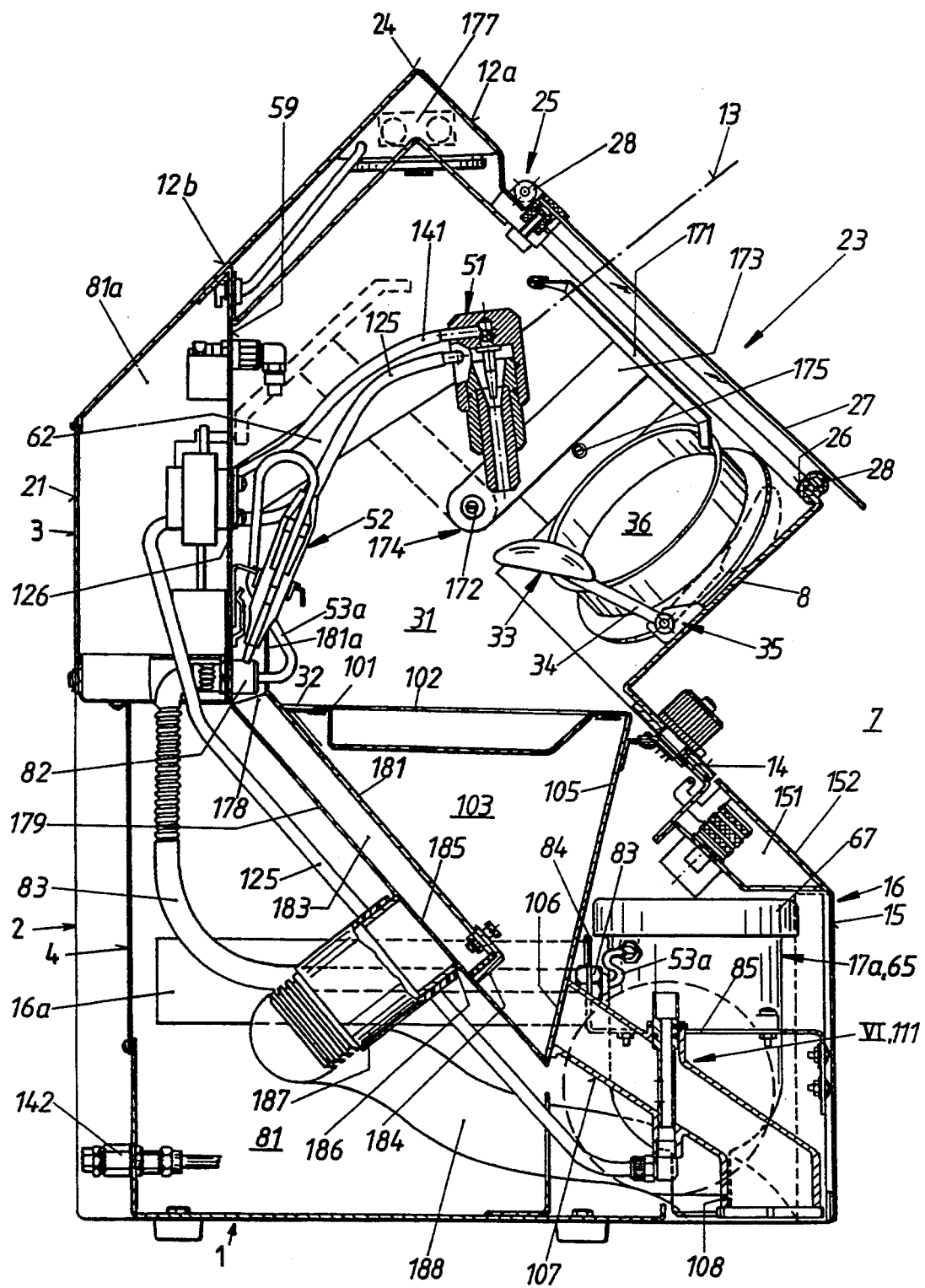
FIG. 2 shows the machining device in side elevation in a vertical section.
Figure 4:
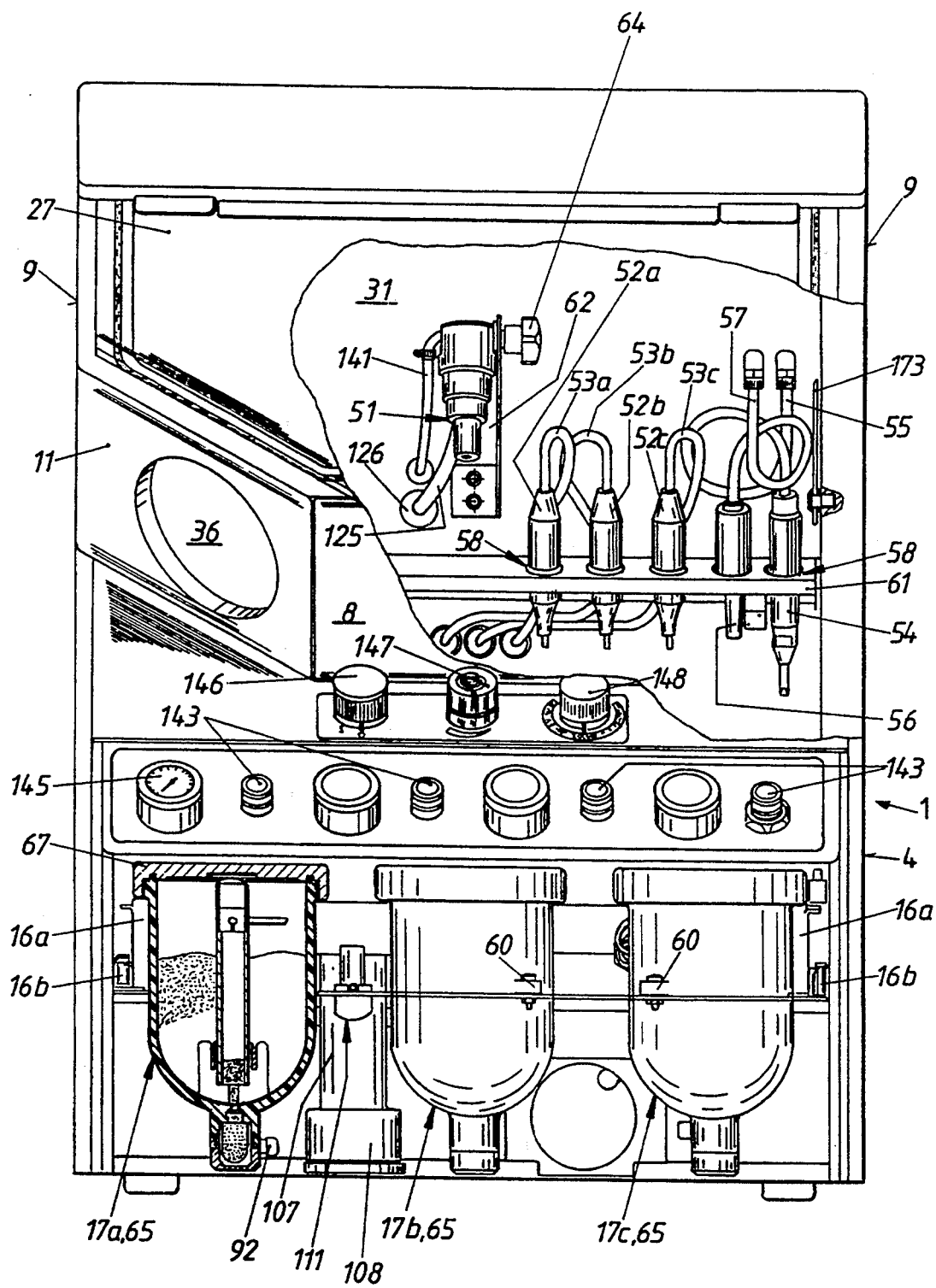
FIG. 4 shows the machining device in a front view, partly sectioned.
Figure 5:
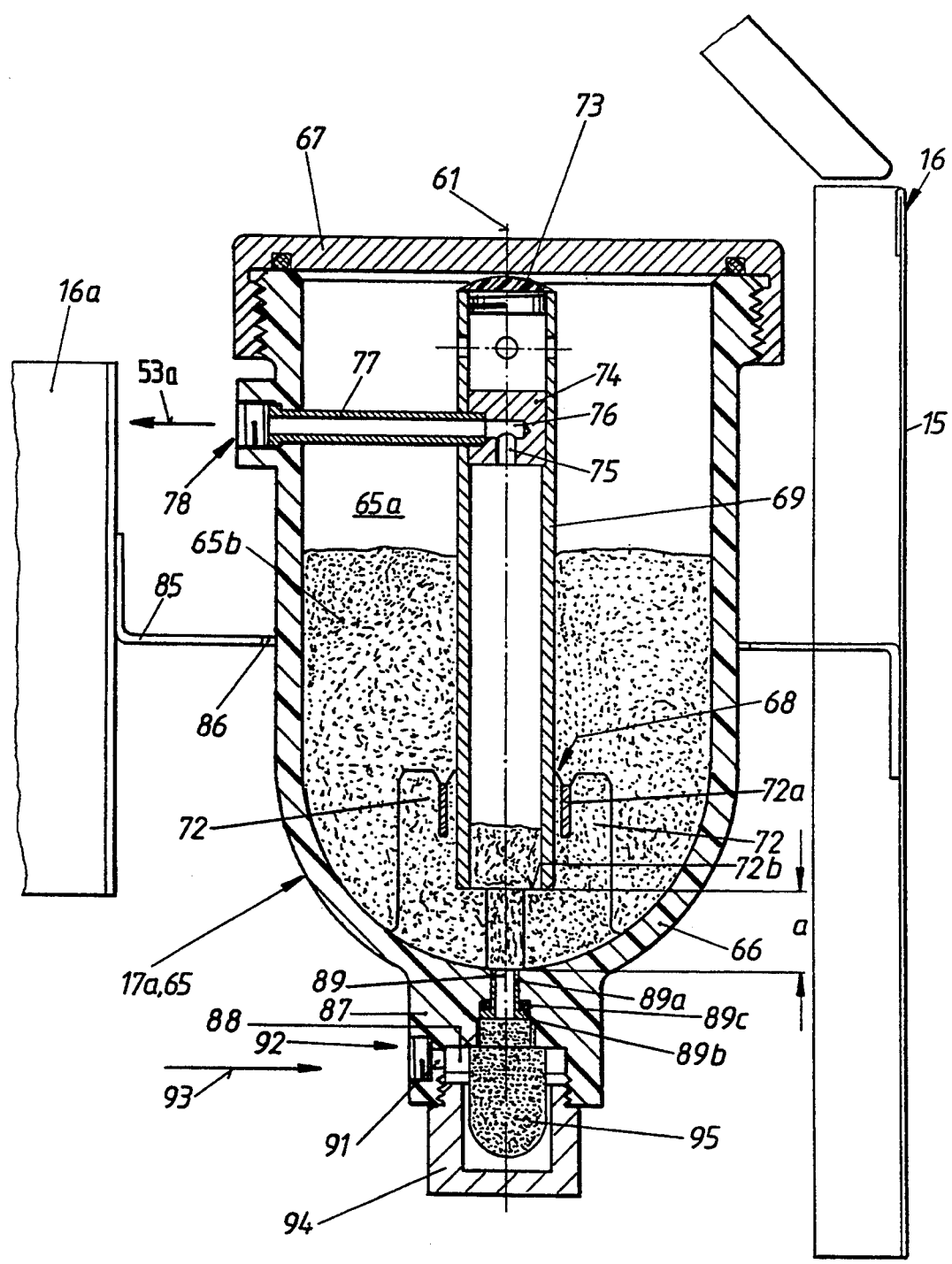
FIG. 5 shows a blasting medium container in vertical half-section in an enlarged representation.
Figure 6:
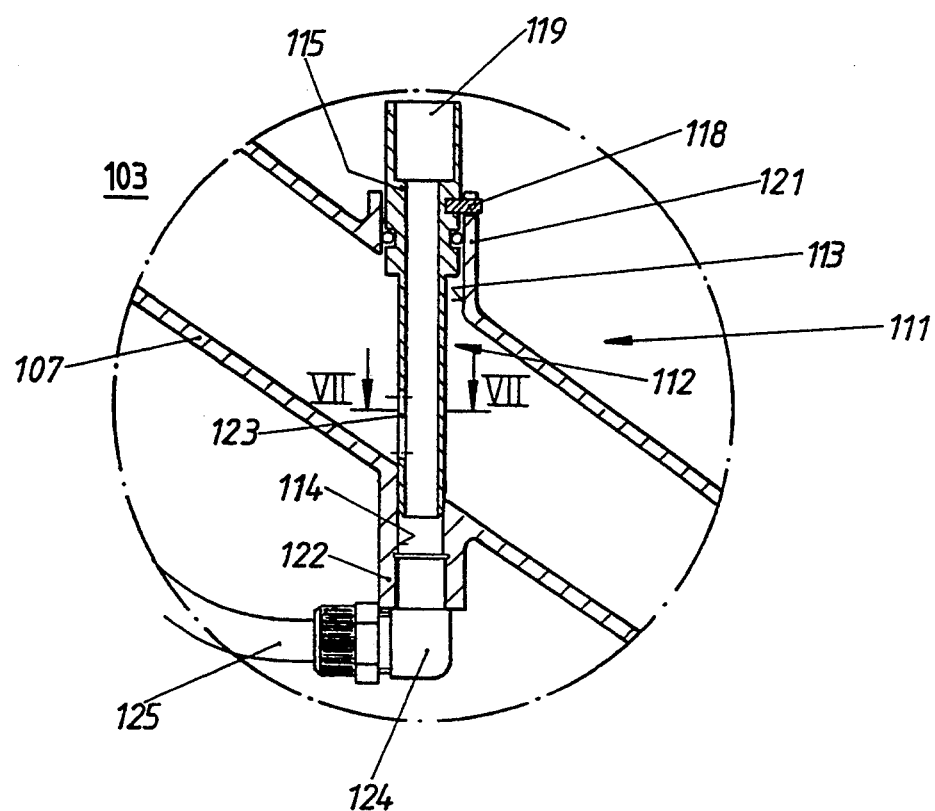
FIG. 6 shows the detail indicated in FIG. 2 by VI, in an enlarged representation.
Figure 7:
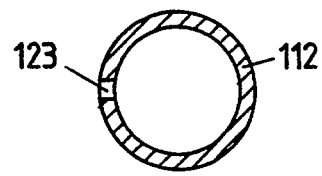
FIG. 7 shows the section VII—VII in FIG. 6.
Figure 8:
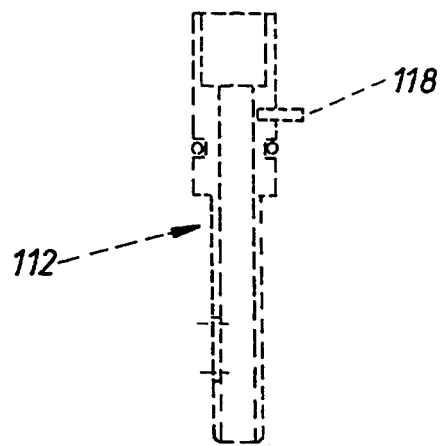
FIG. 8 shows by itself an individual part of the machining device shown in FIG. 6.
Figure 9:
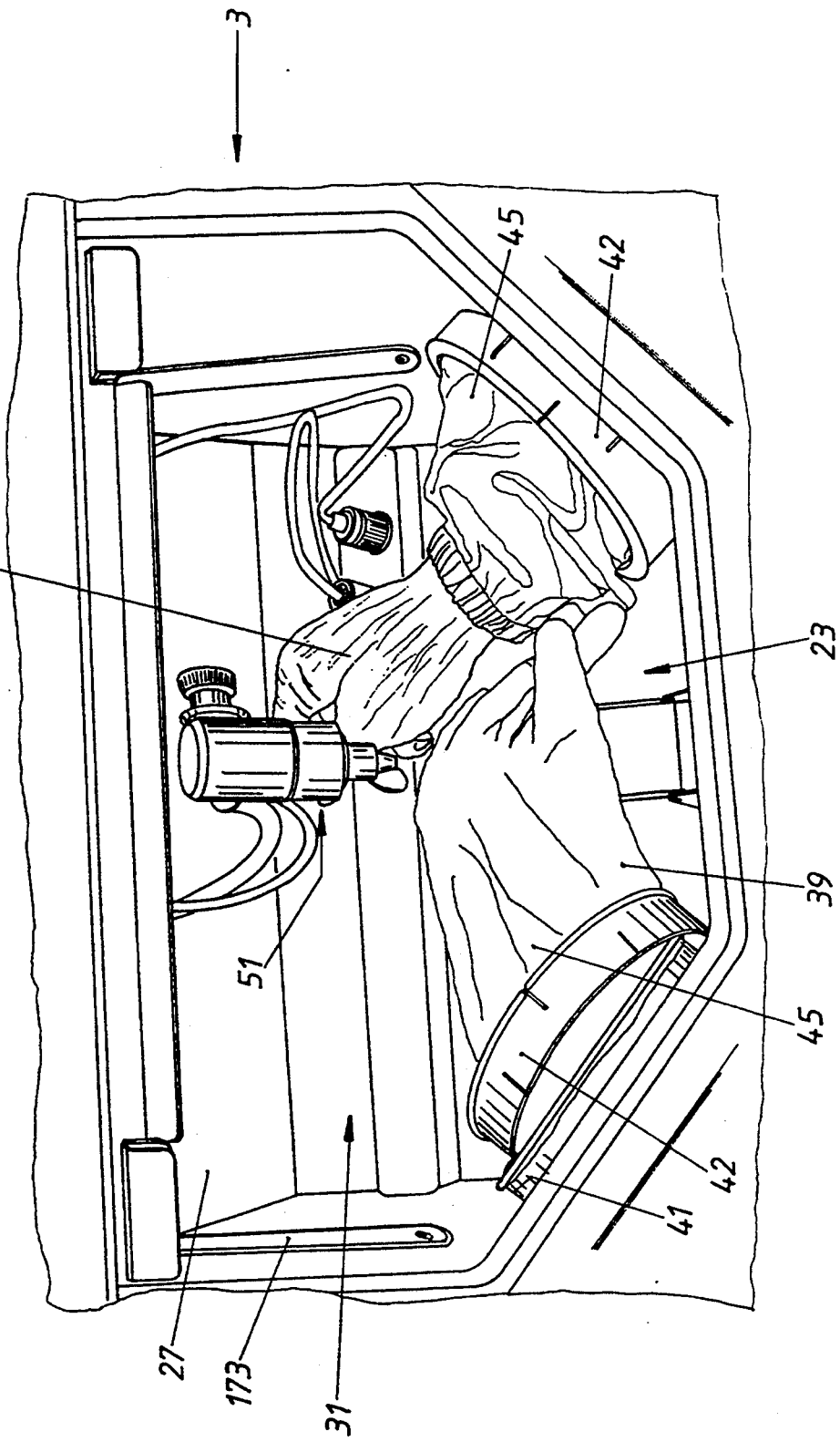
FIG. 9 shows the machining chamber of the machining device looking towards the inspection window.
Figure 10:
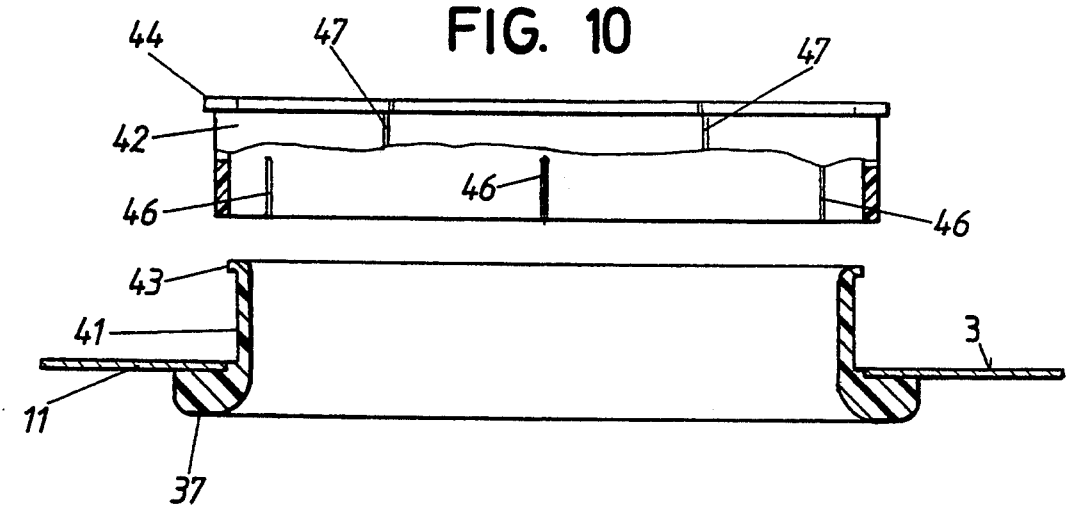
FIGS. 10 and 11 show, in axial section, a clamping device for sleeves or gloves in its clamping position and in its ready-for-mounting position.
Figure 11:
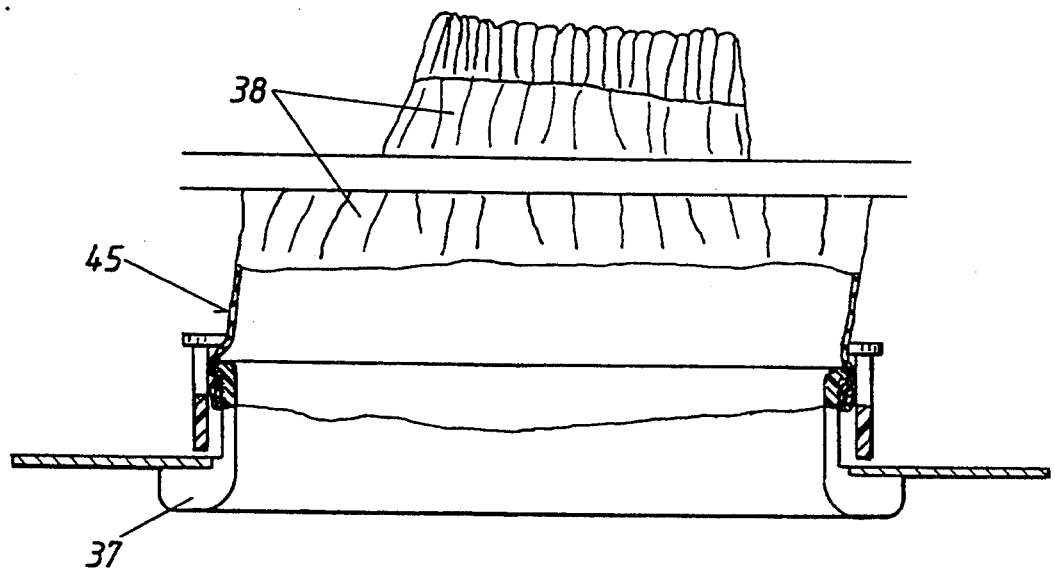

The machining device 1 is designed to be used by a standing person. Its housing 2 is therefore made so tall that its blasting housing 3 is at an ergonomic operating height suitable for standing operation. Beneath the blasting housing 3 the housing 2 is formed as a lower housing 4 for accommodating the individual parts for forming, supplying and removing the blasting medium as well as other parts of the machining device 1. The box-like blasting housing 3 is arranged so that it leans towards the operating side 7 arranged at the front so that, viewed from the side as shown in FIG. 2, the upper end of the blasting housing 3 is roof-shaped and the front wall 8 of the blasting housing 3 extends obliquely upwards towards the operating side 7. In the front lateral edge region the blasting housing 3 is notably flattened off due to the oblique walls 11 extending from the narrowed front wall 8 to the side walls 9. The front wall 8, the side walls 9, the oblique walls 11 and the front and rear top wall 12a, 12b of the blasting housing 3 are arranged in the form of a prism parallel to the forwardly tilted tilt axis 13 of the housing. The oblique front wall 8 with a front part wall 14 of the lower housing 4 extending obliquely in the opposite direction forms a front waist in the housing 2. Beneath the front part wall 14 is the vertical front wall 15 of a drawer 16 in which, parallel to the operating side 7, several, in particular three blasting medium containers 17a, 17b, 17c are arranged. The drawer 16 has respective horizontal drawer rails 16a on either side projecting to the rear which are guided to be moved horizontally in associated guide rails 16b (FIG. 4) fixed on the insides of the side walls 9. The side walls 9 common to the blasting housing 3 and the lower housing 4 and the rear wall 21 merging into the rear top wall 12b are arranged vertically.

In the front top wall 12a is an inspection window 23 which extends downwards from a window upper edge 25 that is spaced from the ridge 24 of the blasting housing 3 and extends laterally up to the periphery of the blasting housing 3 and thus has a hexagonal shape. The inspection window 13 can be opened and closed as desired and includes a window opening 26 in the front top wall 12a that is covered on the outside by a sheet 27 of transparent material, in particular glass, that is mounted in the region of the window upper edges 25 in lateral hinges 28 and can thus be raised and lowered. To seal the inspection window 23, an elastic seal 28 is arranged on the peripheral edge of the window opening 26 on which the weight of the sheet 27 bears. Beneath the rear region of the inspection window 23 in the machining chamber 31, above its intermediate floor 32, is a supporting part 33 for the operator's hands and/or for workpieces to be handled, which in the present configuration is made in the shape of the head of a mushroom with a convexly rounded upper side and is affixed to the free end of a carrying bracket 34 that is pivotably mounted to the blasting housing 3 so that the supporting part 33 is pivotable between the operating position shown in FIG. 2 with continuous lines and the stand-by position shown by broken lines, and is positioned in the respective end positions by its own weight so that unintentional pivoting cannot occur. In the stand-by position the supporting part 33 is located at the edge of the machining chamber 31, preferably before its dead space on the inside of the oblique front wall 8. The mounting 35 for the carrying bracket 34 is preferably arranged on the inside of the front wall 8 and in the present configuration is formed by a plug-in connection into which the carrying bracket 34 can be plugged in and pulled out again as desired in a handy manner, and which provides for pivoting of the carrying bracket 34 between the two end positions. To bound the pivoting movement downwards beyond the operating position, a stop for the carrying bracket 34 is provided in the region of the mounting 35. When not in use the supporting part 33 can thus readily be pivoted upwards into the stand-by position, in which the operating chamber 31 is made free. Because the supporting part 33 can be plugged-in it is not only easy to mount and detach but preferably a plurality of supporting parts 33 of different kinds are available which, depending on the type of workpiece and/or the shape of the workpiece and/or the type of machining to be performed on the workpiece, can be inserted readily into the available mounting fitting.

Manual access to the machining chamber 31 is on the one hand ensured by the open inspection window 23 and on the other hand by two gripping holes 36 which are arranged for ready access one in each front oblique wall 11. The edge of the gripping holes 36 is lined with a rounded lining ring 37. On the inner edges of the gripping holes 36 a glove 38 or sleeve 39 (see FIGS. 9 to 12) can be attached as desired which serves to protect the operator's hands and to seal the gripping holes 36. For the attachment, an easy to use clamping device is preferably provided, comprising a socket piece 41 projecting inwardly from the associated gripping hole 36 and that may be a coaxial extension of the lining ring 40, and a clamping ring 42 that can be pushed from the machining chamber 31 onto the socket piece 41. The socket piece 41 has a small radially projecting clamping elevation 43 on its inner end. To improve the graspability, the clamping ring 42 is likewise provided with a small outwardly projecting elevation 44 on its inner end. The external diameter of the clamping elevation 43 and the internal diameter of the clamping ring 42 are dimensioned one relative to the other so that the clamping ring 42, that diverges slightly conically towards the socket piece 41, can be pushed onto and clamped securely from inside on to the clamping elevation 43 after mounting the free collar edge 45 of the glove 38 or the sleeve 39 on to the socket piece 41. To increase the flexibility and therefore make it easier to handle, the clamping ring 42 has a plurality of peripheral, uniformly distributed longitudinal slits 46 on its end facing the socket piece 41. Longitudinal slits 47 are preferably also provided on the inner end of the clamping ring 42 on the periphery, which can be arranged so that they overlap with the aforementioned longitudinal slits 46, and in this case can be offset from said slits 46 in the peripheral direction. The socket piece 41 and the lining ring 37 and the clamping ring 42 preferably consist of plastics material. To release the glove 38 or the sleeve 39 the clamping ring 42 has only to be pulled off inwardly, using the other hand, after which the glove or sleeve can be pulled off.

Figure 12:
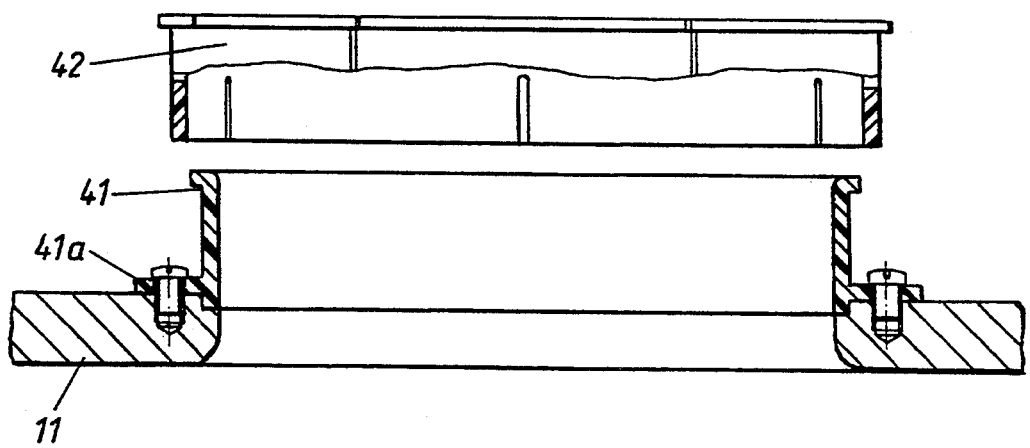
FIG. 12 shows a modified embodiment of a clamping device.

In the configuration shown in FIG. 12 the socket piece 41 is screwed with a flange 41a to the inside of the available hole edge.

The machining device 1 is designed so that several types of machining can be performed on the workpieces, in particular dental workpieces, namely blasting with solid particles, extract from a cast mass (demold), blow off with compressed air. For blasting, at least two blasting nozzles 51, 52 (FIG. 4) are provided of which the one blasting nozzle 51 is arranged so that it is stationary in the upper middle region of the machining chamber 31 spaced above the supporting part 33, and the other blasting nozzle 52 is preferably movable and preferably formed by a blasting pencil that is connected to the associated blasting device by a flexible supply line 53. The stationary blasting nozzle 51 is connected to a circulatory blasting device and the movable blasting nozzle 52 to a one-way blasting device. Preferably three movable blasting nozzles 52a, 52b, 52c are provided that are each connected to their own blasting line 53a, 53b, 53c and their own blasting medium container 17a, 17b, 17c that can be filled with different blasting mediums, e.g. corundum, aluminium oxide ($Al_2O_3$) or glass beads and the like. The movable blasting nozzles 52a, 52b, 52c are each connected to a one-way blasting device.

For demolding (extraction from a cast mass), a chisel 54 is preferably provided, in particular a pneumatic chisel that is connected by means of a flexible supply line 55 to the associated electric or pneumatic supply device. Furthermore an air nozzle 56 is provided that is connected by means of a flexible air line 57 to the existing compressed air device.

Figure 1:
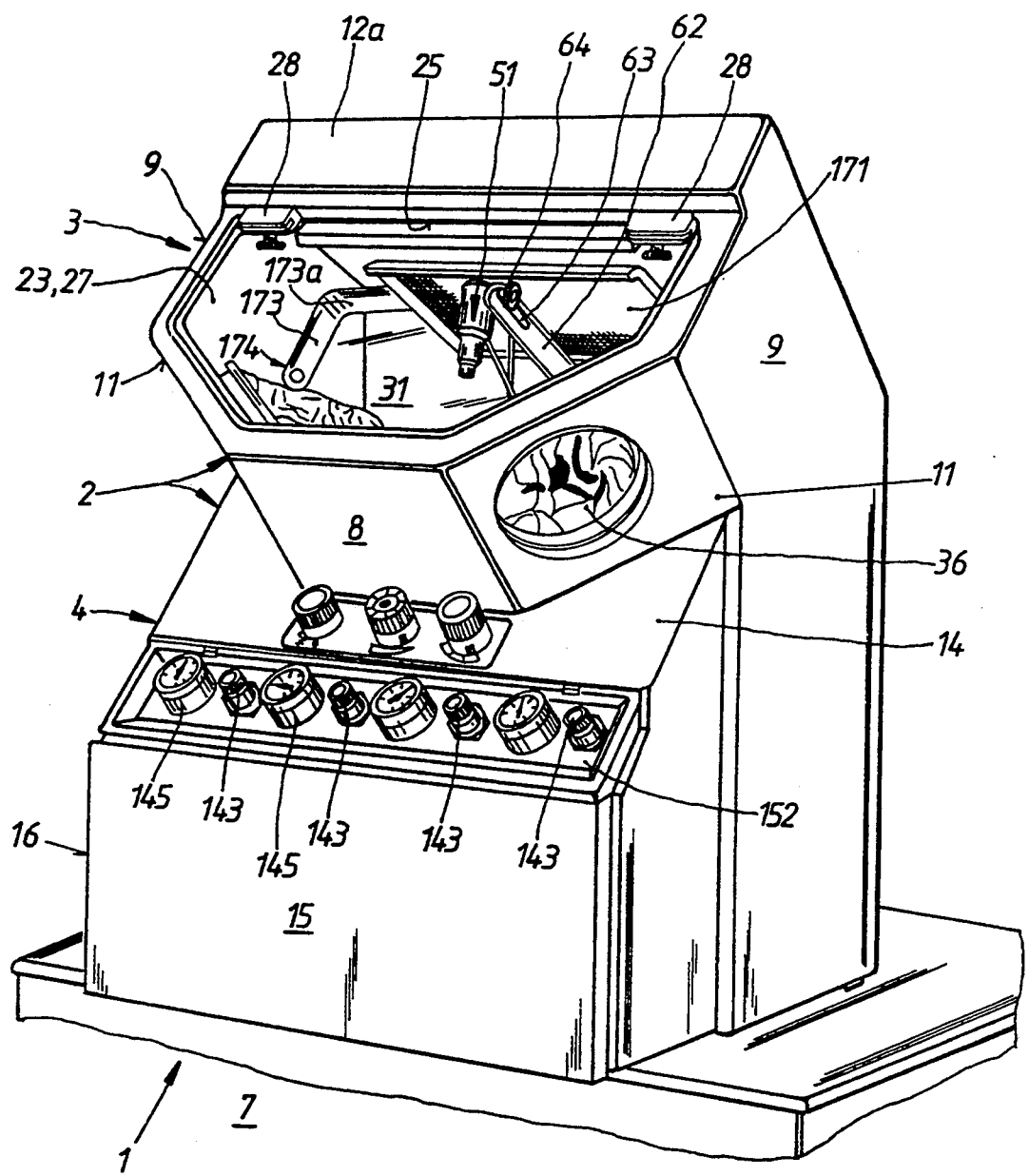
FIG. 1 shows, in a perspective front view, a machining device according to the invention, in particular a machining device for precision, in particular dental, workpieces.

The movable blasting nozzles 52a, 52b, 52c, the chisel 54 and the air nozzle 56 can each be deposited in their respective stand-by positions in a socket fitting which is arranged by means of socket holes 58 in a horizontal multiple socket strip 61 mounted on the inner rear wall 59 of the work chamber 31. Alternatively the chisel 54 can be deposited in its stand-by position beneath the supporting part 33 or in the front region of the blasting chamber 31, preferably on the bottom 32 thereof. The stationary blasting nozzle 51 is mounted on a carrying bracket 62 projecting obliquely upwards from the inner rear wall 59. This stationary blasting nozzle 51 can preferably also be adjusted within a certain range of movement, preferably being movable forwards and backwards and/or pivotable, and securable in the respective position. This purpose can be served by a longitudinal hole 63, shown in FIG. 1, and a securing screw 64 passing through it and being displaceable therein, about the axis of which the blasting nozzle 51, when in the released position, can be pivoted.

Each blasting medium container 17a, 17b, 17c is formed by a preferably circular pot 65 with a spherically rounded pot base 66 and a lid 67 which can be screwed on to the pot 65 and sealed by means of external threads on the upper edge of the pot 65 and internal threads on a cylindrical thread support of the lid 67 (FIGS. 2 to 5). A bayonet catch can also be provided for the lid 67.

In the central base region of the pot base 66 there is a socket 68 for a rising tube 69 to be inserted from the top. Said socket can be formed by three vertical webs 72 arranged around the middle axis 61 of the pot 65 and which are formed integrally with the pot 65 that is preferably made of plastics material. The rising tube 69 extends up to the lid 67 and can be closed at the top by a stopper 73. Spaced beneath the upper end, seated in the rising tube 69, is a feed-through stopper 74 that has an axial passage 75 in its lower region from which a radial passage 76 branches off laterally and into which a radial connecting tube 77 is inserted sealingly. Said connecting tube is connected sealingly at its outer end with a connecting branch 78 screwed into the wall of the pot 65. The associated flexible blasting line 53a, 53b, 53c is connected to the connecting branch 78. The blasting lines 53a, 53b, 53c extend in the hollow space 81 of the lower housing 4 rearwards and upwards into a hollow space part 81a arranged behind the work chamber 31, that space being arranged between the outer and inner rear wall 21 and 59. Here the blasting lines pass through the inner rear wall 59 in a feed-through screw connection 82 (FIG. 2) and they extend further in the work chamber 31 to the associated movable blasting nozzle 52a, 52b, 52c. In the lower housing 4 the blasting lines 53a, 53b, 53c extend in a flexible protective tube line 83 that is connected to the feed-through screw connection 82 and extends towards the associated blasting medium containers 17a, 17b, 17c either to their connecting branches 78 or to a further screw connection 83 that preferably passes through a vertical web 84 that is part of a horizontal mounting rail 85 into which the blasting medium containers 17a, 17b, 17c can each be inserted from the top into a hole 86, in a row parallel to the operating side 7, and can be screwed thereto by means of integral screw projections 60. The mounting rail 85 may preferably be a Z-shaped profile and is fastened in particular inside on the front wall 15 of the drawer 16. The two lateral drawer rails 16a are preferably fastened to the web 84 of the mounting rail 85. Accommodating the blasting lines 53a, 53b, 53c as a hose in the associated flexible protective tube line 83 is advantageous for several significant reasons. The blasting lines 53a, 53b, 53c can quickly and easily be exchanged as they can be pulled out of the associated protective tube line 83 quickly and easily and the new blasting lines can be passed through the protective tube line 83, and this can be done without problems either from the work chamber 31 or from the opened drawer 16. Frequent exchange of the blasting lines 53a, 53b, 53c must be expected as they are naturally subjected to wear. Owing to the flexibility of the blasting lines 53a, 53b, 53c and the protective tube lines 83, the mobility of the drawer 16 is ensured in which the blasting medium containers 17a, 17b, 17c can be moved between a loading position in front of the lower housing 4 (see FIG. 3) and a position inserted into the lower housing 4. Furthermore the protective tube lines also form a protection and protect the lower housing from contaminants when a blasting line bursts.

Formed centrally on the underside of each blasting medium container 17a, 17b, 17c is a material projection 87 into which a blind hole 88 is made from below, and from which a passage extends coaxially upwards into the interior 65a of the associated pot 65, centrally between the webs 72. Extending radially from the blind hole 88 is a passage 91 to which a screw connection 92, that can be screwed into the material projection 87, can be connected. The screw connection is screwed to a supply line 93a, 93b, 93c for compressed air. The blind hole 88 can be closed by a pot-shaped screw-on lid 94. Arranged in the blind hole 88 is an air filter 95a, 95b, 95c that can be screwed into the pot base 66 by a filter foot and which ensures an air passage between the passages 91 and 89. The webs 72 are stabilised in the region of their upper ends by an annular collar 72a that can be injection molded integrally with the webs and the pot 65 or inserted into slits in the webs. The webs 72 are arranged with their inner longitudinal edges at a distance from the middle axis 61 of the pot 65 and at a vertical distance a from the container base 66 and are recessed with appropriate diameter to form a bearing shoulder 72b for the supporting tube 69. The passage 89 is in a sleeve 89a with a flange 89b on its lower end that is sealed by means of an O-ring 89c on an inner shoulder and is supported upwardly. The sleeve 89a is inserted from below into a corresponding hole in the container base 66. Formed in the blasting medium containers 17a, 17b, 17c, that are each an essential functional part of the associated one-way blasting device, is the required air/-blasting medium/mixture which will be described below.

Figure 3:
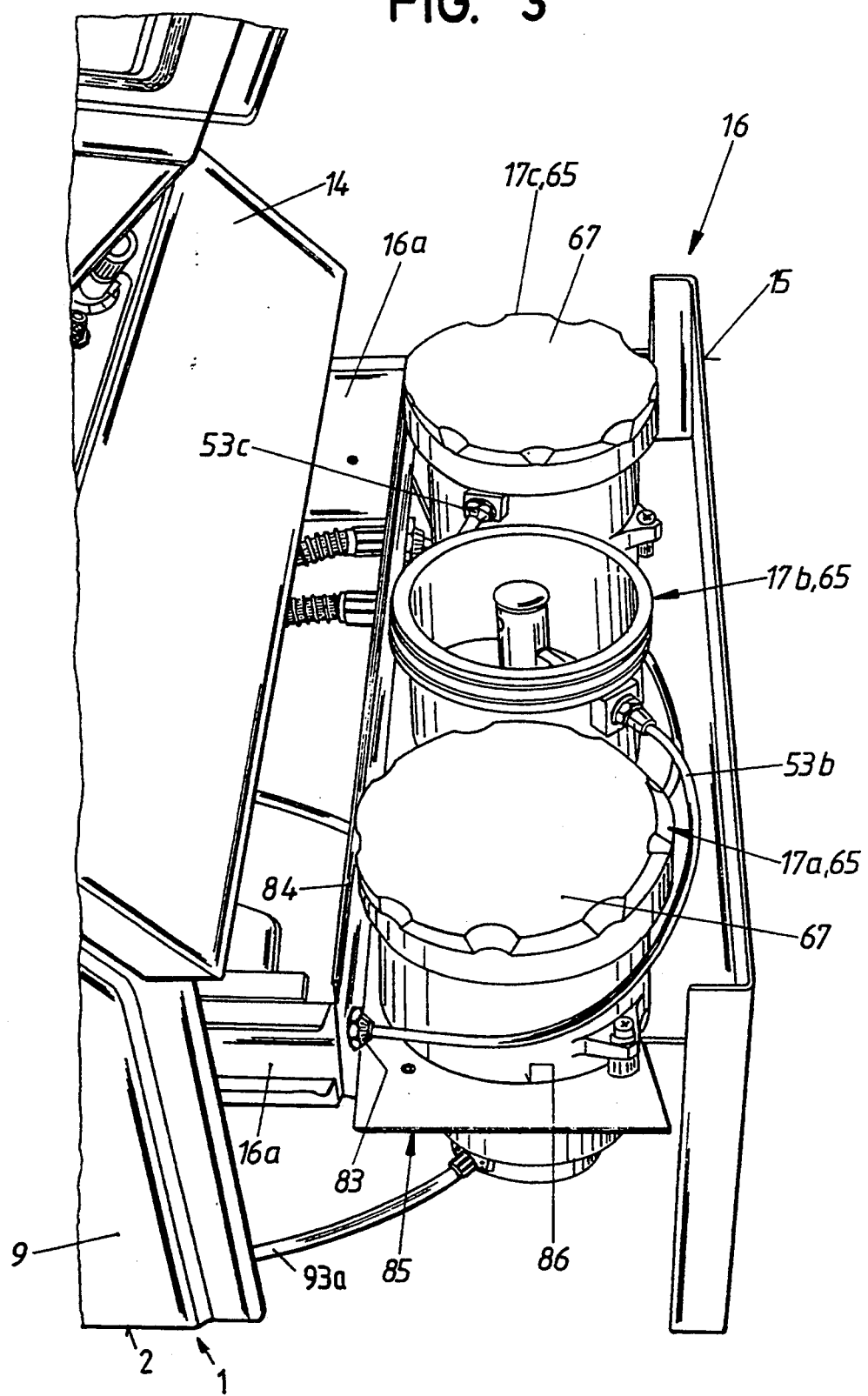
FIG. 3 shows a drawer of the machining device that can be pulled out towards the operating side for accommodating a plurality of blasting medium containers.

To service the blasting medium containers 17a, 17b, 17c to be filled, the drawer 16 is pulled out forwardly whereby the blasting medium containers are moved with it into a position outside the lower housing 4 in which they are easily accessible (FIG. 3). Thereafter the drawer 16 with the blasting medium containers 17a, 17b, 17c is pushed back into the lower housing 4.

Provided in the intermediate floor 32 is a hole 101 in which a sieve 102 is arranged which is permeable to blasting medium and holds back workpiece parts that have been diminished by the blasting medium. Arranged beneath the intermediate floor 32 is a collecting box 103 converging downwardly in the shape of a pyramid. The shape of the collecting box 103 is unsymmetrical to an extent that its downwardly pointing tip—viewed from the operating side 7—is located between two blasting medium containers, here the blasting medium containers 17a, 17b. In the region of the tip there is provided in the front wall 105 of the collecting box 103 a quadrangular outlet hole 106 to which an outlet tube 107 extending obliquely downwards and forwards of appropriate quadrangular cross-section is screwed sealingly by means of a seal. The outlet tube 67 extends obliquely downwards between the blasting medium containers 17a, 17b and in this region is angled vertically downwards in the form of a rounded connecting sleeve 108. A discharge line (not shown) for used blasting medium can be connected to this connecting sleeve 108 by means of a threaded screw connection or a bayonet joint.

The circulatory blasting device having the stationary blasting nozzle 51 employs used blasting medium from the collecting box 103. For this purpose a blasting medium returning device 111 is provided that is connected to the outlet tube 107 and has a receiving tube 112 that is in cross-section preferably circular and which passes transversely, preferably at right angles, in transverse bores 113, 114 through the outlet tube 107. The receiving tube 112 has at its upper end a cylindrical thickening 115 in the lateral surface of which an annular groove is arranged in which there is an elastic sealing ring. Above the annular groove, pressed into a transverse hole, is a retention pin 118 which projects beyond the lateral surface of the thickening 115. The internal cross-section of the receiving tube 112 is widened at its upper end. A filter may, if necessary, be inserted into this widened recess 119. To stabilise the mounting for the receiving tube 112 the transverse bores 113, 114 are arranged in supports 121, 122 formed on the wall of the outlet tube 107. At the upper end of the upper support 121 a slit is provided which accommodates the retention pin 118. The receiving tube 112 is hereby positionally secured against rotation and further displacement downwards. Provided in the region of the free cross-section of the outlet tube 107, on the side of the receiving tube 112 facing the collecting box 103, there is at least one opening 123, preferably in the form of a vertically extending slit which ends at the bottom approximately with the lower inner wall of the outlet tube 107 and through which the used blasting medium from the outlet tube 107 can reach the receiving tube 112. Screwed into the lower support 122, preferably coaxially, is a connection fitting 124 to which a tube line 125 is connected that is in turn connected to the stationary blasting nozzle 51. The tube line 125 extends through the hollow chambers 81, 81a and passes through a feed-through screw connection 126 in the inner rear wall 59. The tube line 125 preferably consists of flexible material in the form of a hose and in the hollow chambers 81, 81a it can be surrounded by a protective tube line that can extend between the connection fitting 124 and the feed-through screw connection 126. As in the case of the blasting lines 53a, 53b, 53c this also ensures quick and ready exchange of the tube line 125.

Figure 13:
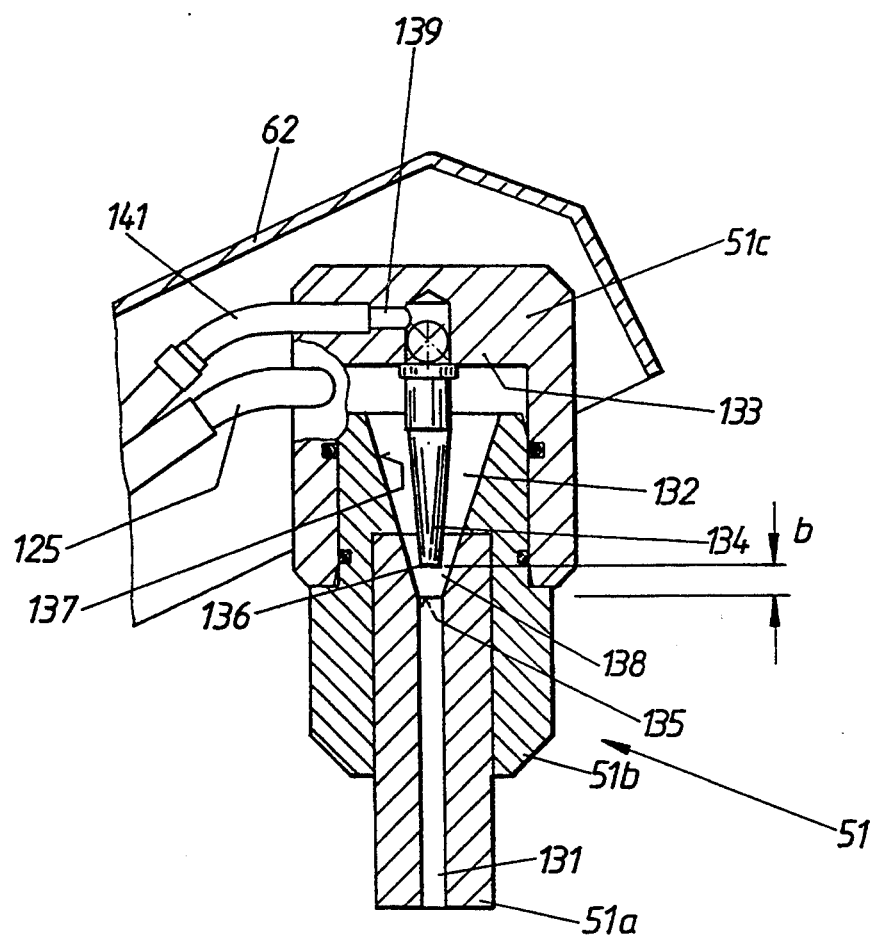
FIG. 13 shows, in axial section, a blasting nozzle for circulatory blasting.

The stationary blasting nozzle 51 has, as shown in FIG. 13, an axial nozzle passage 131 that extends from an injection chamber 132 converging, preferably in the shape of a cone, towards the nozzle tip. The tube line 125 is radially connected sealingly by means of a line connection in the end region of the injection chamber 132 remote from the nozzle. In a transverse wall 133 of the blasting nozzle 51 bounding the injection chamber 132 on the side remote from the nozzle tip, a tubular inner nozzle 134 that is coaxial to the nozzle passage 131 and the injection chamber 132 is inserted securely with a foot into a receiving hole, and extends to just before the front end of the converging injection chamber 132 and is spaced a distance b of a few millimeters from the inlet hole 135 of the nozzle passage 131. There is a small annular gap 138 between the preferably cone-like tapered front end 136 of the inner nozzle 134 and the converging inner lateral surface 137 of the injection chamber 132. The inner nozzle 134 is connected to a supply passage in the transverse wall 133 to which a preferably flexible compressed air supply line 141 is connected by means of a, if necessary, radial connecting passage 139. Said supply line extends, e.g., from the hollow chamber 81a and passes through the inner rear wall 59 in a feed-through screw connection and is connected to the existing compressed air supply of which only the feed-through connection 142 (FIG. 2) arranged in the lower region of the rear wall 21 is indicated schematically. The nozzle passage 131 is preferably arranged in a cylindrical nozzle tube 51a that is inserted securely from the front into a nozzle insert 51b. The nozzle tube 51a overlaps the front end 136 of the inner nozzle 134 with a conical passage section which forms the front part of the injection chamber 132. The nozzle insert 51b is inserted, preferably axially displaceably, from the front into a nozzle holding body 51c, and retained there and sealed, with a space between the transverse wall 133 and the nozzle insert 51b.

Figure 14:
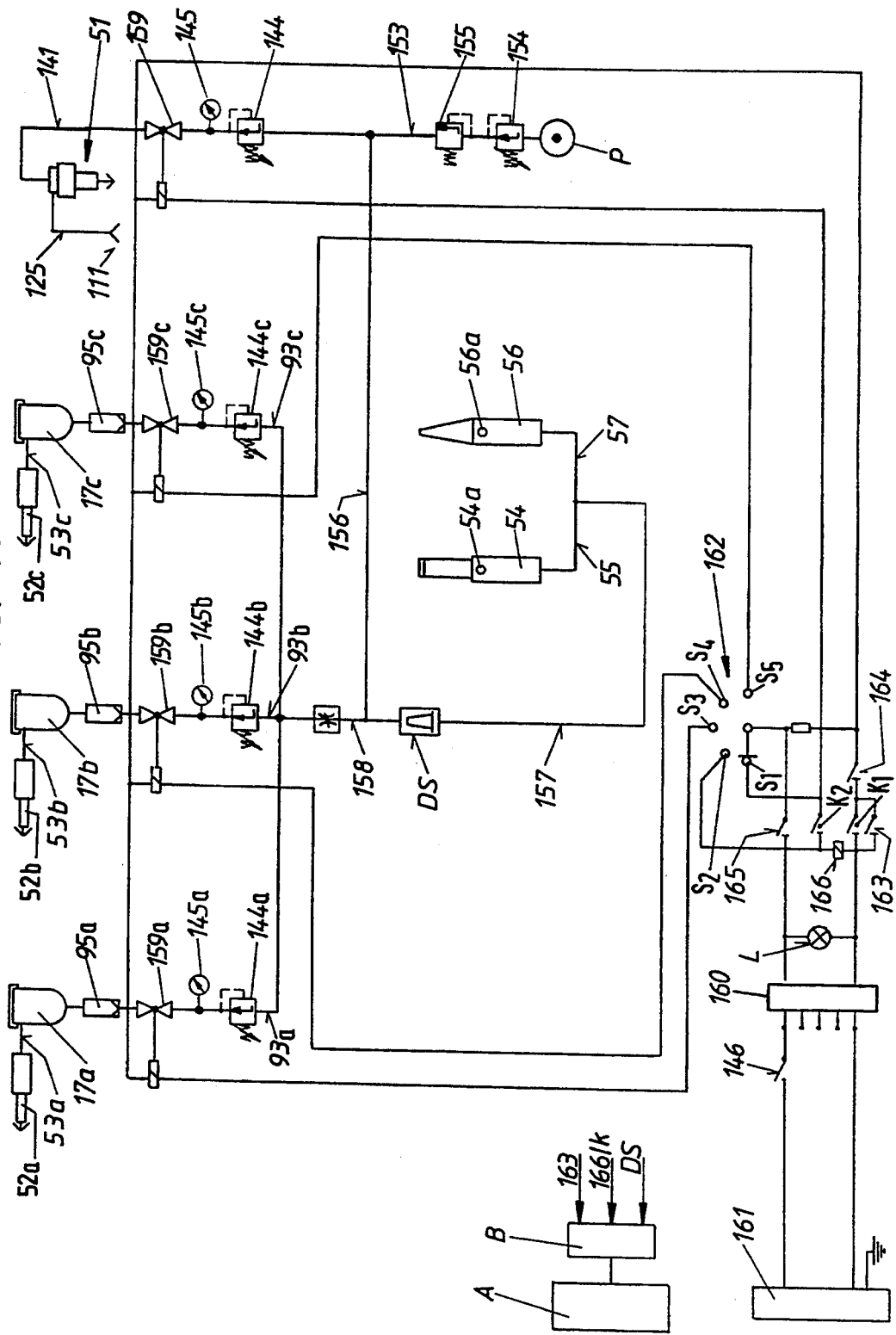
FIG. 14 shows an electro-pneumatic control plan for a machining device according to the invention formed as a machining device.

To control the machining device 1 four setting members 143 (FIG. 4) in the form of control knobs are provided with which the compressed air can be set in a particular setting range in each of the four existing blasting devices via pressure controls 144 (shown only in FIG. 14). The respective pressures are indicated by four manometers 145 that are connected to the associated compressed air line sections. In addition three further setting members 146, 147, 148 are provided, the function of which will be described below. The setting members 143 and the manometer 145 are preferably arranged in a lower and the setting members 146, 147, 148 in an upper horizontal row on the oblique front part wall 14, wherein the lower row is preferably arranged in a horizontal trough-shaped depression 151 that can be closed by a hinged cover 152.

The control and operation of the machining device 1 will now be described with reference to the control plan shown in FIG. 14. The compressed air produced by a compressed air source P external or internal to the device is available at an inlet tube line 153 in which a pressure controller 154 that can be adjusted by a setting member 147 and a safety valve 155, are arranged one behind the other in the direction of flow. The inlet tube line 153 branches into the supply line 141 which leads to the stationary blasting nozzle 51, and a branch line 156 that branches off into two further branch lines 157, 158. Arranged in the supply line 141 in the direction of flow of one of the already described pressure controllers 144 are the associated manometer 145 and an electromagnetic shut-of valve 159. A through-flow sensor DS is arranged in the branch line 157. The two flexible supply lines 55 and 57 for the chisel 54 and the air nozzle 56 branch from the branch line 157. The branch line 158, in which a preferably adjustable throttle is arranged, branches off into the three supply lines 93a, 93b, 93c that are connected to the associated blasting medium containers 17a, 17b, 17c and in which respective pressure controllers 144a, 144b, 144c which can be acted upon by the associated setting members 143, the associated manometers 145a, 145b, 145c, associated electromagnetic shut-off valves 159a, 159b, 159c and associated air filters 95a, 95b, 95c are arranged in the direction of flow one behind the other. The chisel 54 and the air nozzle 56 each have a manually operable switching element 54a, 54b for switching them on and off.

The operation will now be described with reference to the electric circuit arrangement of the control arrangement.

The primary side of a mains transformer 160 is connected to the mains via a main switch 146a. There is a control lamp L by the two output connections on the secondary side of the mains transformer 160 which lights up when the main switch 146a is closed.

Also connected to the output of the mains transformer 160 are a locking relay 166 with self-locking contacts $K_1$ and $K_2$, a foot switch 163, two switches 164 and 165, and a changeover or selector switch 162 that can be controlled by the setting member 148. The switch 164 is closed when the drawer 16 is pushed in. The switch 165 is closed when the inspection window 23 is closed.

The connection of the above-mentioned electrical elements can be seen in FIG. 14 and will not be described in detail. Only the function will described.

It will be assumed that the selector switch 162 is initially located in the switching position $S_1$. When the main switch 146a and the foot switch 143 are closed, the magnet valve 159 for the blasting nozzle 51 is opened whereby the blasting nozzle 51 is put in operation for as long as the foot switch 143 is closed.

When, with a closed main switch 146a, the selector switch 162 is moved into the switching position $S_2$, the relay magnet 166 is energised and the self-locking contacts $K_1$, $K_2$ are closed. The magnet valve 159 is hereby opened and the blasting nozzle 51 is set to continuous operation.

When, with a closed main switch 146a, the selector switch 162 is switched over to the switching position $S_3$ the magnet valve 159a for the blasting nozzle 52a is opened on closing the foot switch 163. When the foot switch 163 is released again the magnet valve 159a for the blasting nozzle 52a is closed again.

When the selector switch 162 is in the switching position $S_4$ the magnet valve 159b is opened when the main switch 146a is closed and the blasting nozzle 52b is thus set in operation.

When the selector switch 162 is in the switching position $S_5$, the magnet valve 159c is opened and the blasting nozzle 52c is set in operation when the main switch 146a and the foot switch 163 are closed.

When the drawer 16 and the inspection window 23 are closed the blasting device, preset by the selector switch 162, can thus be put into operation by operating the foot switch 163.

The machining device 1 is suitable for surface treatment of precision workpieces of different kinds, in particular in the jewellery industry, archaeology, general mechanical engineering and in particular for dental workpieces. The machining device 1 is not only suitable for blasting by means of granular blasting mediums but also for demolding and/or blowing off with compressed air the workpieces or the part to be treated. By means of blasting, surface cleaning, and surface conditioning to increase surface area and the adherence of a coating can be carried out. This is of particular importance in the case of dental workpieces. In particular, in the manufacture of dental cast parts, the removal of the remainder of the embedding mass can be carried out. For blasting both the substantially fixed blasting nozzle 51 or one of the freely movable blasting nozzles 52a, 52b, 52c or blasting pencils can be used, and the desired blasting medium or the desired granular size can be selected. Circulatory or one-way blasting can be selected.

Precisely directed working of the available workpiece can be effected with the freely movable blasting nozzles. A particular requirement for dental crowns is, for example, that the inner edges of the crown edge must have a sharp edge in order that, after the crown has been mounted on the crown edge a tight connection is provided to prevent the access of bacteria. This can be achieved in particular by precisely directed blasting by means of movable blasting nozzles. In particular in the case of dental cast parts, the cast part can be extracted from the cast in the machining device before blasting, for which purpose electrically or pneumatically operable extracting tools are provided. In the present exemplary embodiment the pneumatic chisel 54 is provided. Depending on the condition of the extracted cast piece, remains of the casting mass can subsequently be removed by blasting, and blowing out or blowing off of the position to be machined or thoroughgoing blowing out or blowing off can be effected.

On switching on the circulatory blasting device with the blasting nozzle 51, compressed air flows through the supply line 141 and the inner nozzle 134 and injects a suction air flow in the region of the annular gap 138 into the tube line 125. Because of this suction air flow blasting medium in the outlet tube 107 is sucked in through the slit 123 and transported through the suction air flow to the tip of the inner nozzle 134, where the compressed air, the suction air and the blasting medium mix together and emerge as a compressed air flow through the blasting nozzle 51. The blasting nozzle 51 functions as an injector system. Due to physical effects fluctuations in the compressed air flow can arise so that an intermittent (pumping) blasting action can occur. It has been found that as a result of the suction due to withdrawal of air at the rear end of the receiving tube 112 a uniform flow of air and as a result a uniform blasting effect is achieved. The uniform flow of air also leads to homogenous fluidisation of the blasting medium sucked into the slit 123 which contributes to a homogenous blasting effect. In the case of circulatory blasting a blasting medium is used of which the composition is dependent upon the previous blasting treatment because the blasting medium used in a previous blasting treatment collects in the collecting box 103 and can thus include a blasting medium mixture.

On switching on a one-way blasting device, which in the present exemplary embodiment can be provided with three different blasting medium types, unused blasting medium is supplied in each case to the respective blasting nozzle 52a, 52b, 52c. The selected compressed air supply line 93a, 93b, 93c is put in operation by opening the associated shut-off valve 159a, 159b, 159c. Owing to the compressed air flow flowing from the passage 89 upwards into the interior 65a of the associated blasting medium container 17a, 17b, 17c the blasting medium 65b therein is fluidised above the pot base 66 and in the rising tube 69 and carried upwards, with this compressed air-blasting medium mixture supplied through the blasting lines 53a, 53b, 53c to the associated blasting nozzles 52a, 52b, 52c. It has become apparent that this fluidisation is not dependent on the filling level of the blasting medium in the blasting medium container. A uniform flow of the compressed air-blasting medium mixture can thus be produced independently of the filling level.

Blasting is carried out at air pressures between 1.5 and 6 bar depending on the type of blasting medium and its granular size.

Demolding, blowing off and/or blasting of the workpieces is carried out with the operator's hands inserted through the gripping holes 36 into the work chamber 31. The supporting part 33 has proved itself to be an advantageous support for the hands and/or the workpiece, so that faulty treatment of the workpiece caused by unsteady hands can be prevented.

In particular in the case of intensive blasting, as with circulatory blasting, which operates with higher pressures and greater blasting medium throughput, action on the inspection window sheet 27 can hardly be avoided. Action on the sheet 27 is undesirable as the glass becomes worn, dull and opaque. The sheet 27 is therefore preferably provided on the inside with a transparent coating of wear-resistant material. This coating is also advantageous for preventing accidents because if the sheet should break, the coating holds the broken pieces of the sheet together.

Furthermore a protective sieve 171 of metal or plastics material is provided inside to protect the sheet 27. The sieve can be swivelled between a working position near the front of the sheet 27 (shown in FIG. 2 by continuous lines) and a stand-by position which leaves the inspection window 23 free (indicated by broken lines in FIG. 2). The protective sieve 171 is positioned in its respective swivelled end positions by stops against which it bears due to its weight. Self-induced movement is therefore impossible. The swivel axis 172 of the protective sieve 171 extends preferably parallel to the operating side 7, substantially horizontally in the middle region of the work chamber 31 so that the protective sieve can be swivelled from its working position located in the front region of the work chamber at the top into a stand-by position located in the rear region of the work chamber 31 at the top. The protective sieve 171 is fastened to lateral carrying limbs 173 which extend on the inside near the side walls 9 of the blasting housing 3, each to a respective swivel bearing 174 that is fastened to the associated side wall 9 and arranged in the region of the swivel axis 172. Said limbs are arranged to swivel in said bearings. The preferably flat carrying limbs 173 arranged parallel to the side walls 9 may be made angled at their upper limb arms 173 (FIG. 1) if the protective sieve 171 is substantially smaller than the width of the work chamber 31. The protective sieve 171 is arranged so that it is central to the stationary blasting nozzle 51 and preferably also central to the work chamber 31. The swivel bearings 174 are preferably formed by bearing pins and associated bearing bores that can be arranged on the carrying limbs 173 or on the side walls 9. The carrying limbs 173 are preferably biased outwardly in their bearing position and can be bent inwards elastically to release them from or reinsert them into the swivel bearings 174 in a ready and simple manner. In this way the protective sieve 171 can be mounted and dismounted simply and quickly and exchanged in a ready manner in case of wear. For positioning in the working position a stop 175 can be provided on at least one side wall 9 against which, in the associated oblique position of the protective sieve 171, the carrying limb 173 bears under its own weight. In the stand-by position, in which the protective sieve 171 is swivelled over the fixed blasting nozzle 51 and its bracket (62), the protective sieve 171 can be restricted by the rear wall 79 of the work chamber 31 or by the bracket 62 acting as a stop.

The housing 2, or the blasting housing 3 and the lower housing 4 can be made of plastics material and are preferably foamed, e.g. of polyurethane (PU), or they can be made of metal, in particular sheet steel. To light the working chamber 31 one or two lighting arrangements having tubular lamps are provided on the inside in the top ridge region.

When the machining device 1 is in operation compressed air is delivered continuously into the work chamber 1 when using the blasting arrangements, the pneumatic chisel 54 and the air nozzle 56, and during treatment of the workpiece particles or dust from the material of which it is made, e.g. quartz or health hazardous materials, arrive in the work chamber 1. A suction opening is therefore associated with the machining chamber 31 through which suction can take place, through the work chamber 31 by means of a suction device A (only indicated in FIG. 14), which is switched on and off electrically automatically by means of an Or-member B with the operation of the foot switch 163, the self-locking relay 166 and a through flow sensor DS carrying out a switching function, i.e. in dependence upon the operation of the blasting arrangements, the chisel 54 or the air nozzle 56. The suction device A has a separator for particles and dust. The through-flow sensor DS is arranged in the hollow part 81.

The suction opening is formed by a suction slit 178 in the intermediate floor 32 on its rear end. The length of the suction slit 178 can correspond to or be smaller than the width of the intermediate floor 32. A partition wall 181 extends from the rear edge of the intermediate floor 32, parallel to the rear wall 179 of the collecting box 103, to near the lower end of the collecting box 103, and extends to the oblique side walls 182 of the collecting box 103 and thus bounds a suction shaft 183 extending downwards from the suction slit 178. Said suction shaft is closed at the bottom by a bottom wall 184 connecting the lower edge of the partition wall 181 to the rear wall 179. Since the side walls 182 also laterally bound the suction shaft 183, it converges likewise downwards.

To prevent blasting medium from falling from the intermediate floor 32 into the suction slit 178 a web wall 181a is arranged on its front edge which extends laterally to the side walls 9 and upwards to about the middle working chamber height and surrounds the suction slit laterally or extends up to the side walls. The suction shaft is hereby extended upwards beyond the intermediate floor 32. The blasting nozzles 52a, 52b, 52c when in their sockets and possibly the air nozzle 56 when in its socket, preferably project into the extended suction shaft 183.

Provided above the bottom wall 184, in the rear wall 179 is a, preferably circular, hole 185 from the edge of which a connecting sleeve 186 extends downwards and to the rear. A suction hose 188 can be mounted to and clamped to the connecting sleeve 186 by means of a socket piece 187. Said suction hose 188 extends to the front region of the lower housing 4 and, for example, between the second and third blasting medium containers 17b, 17c where, in the region of the drawer 16, there is no bottom wall of the housing. From here the suction hose 188 extends downwards and it can form a socket piece for a suction hose section of the suction device A to be connected thereto.

What is claimed is:

1. A device for machining workpieces said device comprising:

a housing defining a chamber for workpieces to be machined, there being an inspection window on the housing to allow viewing of the housing chamber;

first and second spaced gripping holes defined in the housing;

first and second gloves associated one each with the first and second gripping holes, at least one of said gloves including a free collar edge region;

means for mounting the at least one glove to the housing around the gripping hole, wherein the mounting means includes a first and a second coaxial clamping ring with the first coaxial clamping ring insertable into the second coaxial clamping ring to capture the free collar edge region of the at least one glove between the first and second clamping rings, said clamping rings being formed by short sleeve members;

means for affixing one of the first and second clamping rings to the housing around the gripping hole; and the other one of the first and second clamping rings being movable relative to the one clamping ring, the movable clamping ring having inner and outer circumferential ends with circumferentially-spaced slits axially extending from both the inner and the outer ends to approximately the mid-point between the inner and the outer circumferential ends, whereby the slits on the inner end are laterally offset from the slits on the outer end and the inner circumferential end slits and outer circumferential end slits extend past the midpoint between the inner and outer circumferential ends to be in overlapping relation to one another.

2. A device for machining workpieces said device comprising:

a housing defining a chamber for workpieces to be machined, there being an inspection window on the housing to allow viewing of the housing chamber;

first and second spaced gripping holes defined in the housing;

first and second gloves associated one each with the first and second gripping holes, at least one of said gloves including a free collar edge region;

means for mounting the at least one glove to the housing around the gripping hole, wherein the mounting means includes a first and a second coaxial clamping ring With the first coaxial clamping ring insertable into the second coaxial clamping ring to capture the free collar edge region of the at least one glove between the first and second clamping rings; and means for affixing one of the first and second clamping rings to the housing around the gripping hole, wherein said affixing means includes a portion of said affixed clamping ring extending through the housing to the exterior thereof with the portion comprising an external flange, said flange being affixed to the housing around the gripping hole.

3. A device for machining workpieces said device comprising:

a housing defining a chamber for workpieces to be machined, there being an inspection window on the housing to allow viewing of the housing chamber;

first and second spaced gripping holes defined in the housing;

a glove associated with each gripping hole wherein said glove includes a free collar edge region;

means for mounting the at least one glove to the housing around the gripping hole, wherein the mounting means includes a first and a second coaxial clamping ring with the first coaxial clamping ring insertable into the second coaxial clamping ring to capture the free collar edge region of the at least one glove between the first and second clamping rings with the clamping rings being formed by short sleeve members;

means for affixing one of the first and second clamping rings to the housing around the gripping hole;

the other one of the first and second clamping rings being movable relative to the one clamping ring and includes an inner peripheral surface which diverges conically towards the affixed clamping ring.

4. A machining device according to claim 3 wherein the affixed clamping ring has an inner end projecting into the housing with a radially outwardly projecting clamping elevation on the inner end of the affixed clamping ring.

5. A machining device according to claim 3 wherein the clamping ring has an inner end projecting into the housing with the inner end including a gripping elevation.

6. A machining device according to claim 3 wherein the movable coaxial clamping ring has inner and outer ends with circumferentially-spaced slits axially extending from the outer end to approximately the mid-point between the outer end and the inner end of the movable coaxial clamping ring.

7. A machining device according to claim 3 wherein the movable coaxial clamping ring has an inner end extending into the housing and an outer end and includes circumferentially-spaced slits axially extending from the inner end to approximately the mid-point between the inner end and the outer end of the movable clamping ring.

8. A machining device according to claim 3 wherein the first and the second coaxial clamping ring are formed from one of either a metal or a plastic.

9. A machining device according to claim 3 wherein the affixed clamping ring is screwably fastened to the housing around the gripping hole.

10. A device for machining workpieces said device comprising:

a housing defining a chamber for workpieces to be machined, there being an inspection window on the housing to allow viewing of the housing chamber;

first and second spaced gripping holes defined in the housing;

first and second gloves associated one each with the first and second gripping holes, at least one of said gloves including a free collar edge region;

means for mounting the at least one glove to the housing around the gripping hole, wherein the mounting means includes a first and a second coaxial clamping ring with the first coaxial clamping ring insertable into the second coaxial clamping ring to capture the free collar edge region of the at least one glove between with the first and second clamping rings with said clamping rings being formed by short sleeve members; and means for affixing one of the first and second clamping rings to the housing around the supply hole; and the other one of the first and second clamping rings being movable relative to the one clamping ring with the movable clamping ring having inner and outer circumferential ends with circumferentially-spaced slits axially extending from both the inner and outer ends.

11. A device for machining workpieces, said device comprising:
    a housing defining a chamber for workpieces to be machined, there being an inspection window on the housing to allow viewing of the housing chamber;
    a gripping hole defined in the housing;
    a glove associated with the gripping hole said glove including a free collar edge region;
    means for mounting the glove to the housing around the gripping hole,
    wherein the mounting means includes a first and second coaxial clamping ring with the first coaxial clamping ring insertable into the second coaxial clamping ring to capture the free collar edge region of the glove between the first and second clamping rings; and
    means for affixing one of the first and second clamping rings to the housing around the gripping hole,
    the other one of the first and second clamping rings being movable relative to the one clamping ring with the movable clamping ring having axially spaced inner and outer ends with circumferentially spaced slits extending axially from one of the inner circumferential end and the outer circumferential end.

12. An apparatus for mounting a glove within a hole defined in a housing for accessing a chamber in a housing, the apparatus comprising:
    a glove including a free collar edge region;
    means for mounting the glove to a housing around a hole in the housing,
    wherein the mounting means includes a first and a second coaxial clamping ring with the first coaxial damping ring insertable into the second coaxial clamping ring with the first and second clamping rings coaxially aligned to capture the free collar edge region of the glove between the first and second clamping rings; and
    means for affixing one of the first and second clamping rings to a housing around a hole in the housing,
    the other one of the first and second clamping rings being movable relative to the one clamping ring and including an inner peripheral surface which tapers in an axial direction.

* * * * *